US008893721B2

(12) United States Patent
Futrell, Jr.

(10) Patent No.: US 8,893,721 B2
(45) Date of Patent: Nov. 25, 2014

(54) SURGICAL DRAPE WITH VAPOR EVACUATION

(71) Applicant: Futrell Medical Corporation, Los Angeles, CA (US)

(72) Inventor: James W. Futrell, Jr., Los Angeles, CA (US)

(73) Assignee: Futrell Medical Corporation, Los Angeles, CA (US)

( * ) Notice: Subject to any disclaimer, the term of this patent is extended or adjusted under 35 U.S.C. 154(b) by 0 days.

(21) Appl. No.: 13/836,918

(22) Filed: Mar. 15, 2013

(65) Prior Publication Data

US 2014/0261458 A1    Sep. 18, 2014

(51) Int. Cl.
*A61B 19/08*    (2006.01)

(52) U.S. Cl.
CPC .................................. *A61B 19/088* (2013.01)
USPC ....................................................... 128/853

(58) Field of Classification Search
CPC .... A61B 19/08; A61B 19/087; A61B 19/088; A61B 19/10; A61B 19/12; A61F 13/00029; A61F 13/00021; A61F 13/00034; A61F 13/00068; A61M 1/0088; A61M 27/00
USPC .......... 128/846, 849–856; 602/47; 5/821, 823
See application file for complete search history.

(56) References Cited

U.S. PATENT DOCUMENTS

| | | | | |
|---|---|---|---|---|
| 2,305,289 A * | 12/1942 | Coburg | ......................... | 128/850 |
| 3,763,857 A * | 10/1973 | Schrading | ..................... | 128/853 |
| 4,136,222 A | 1/1979 | Jonnes | | |
| 4,323,069 A | 4/1982 | Ahr et al. | | |
| 4,848,364 A * | 7/1989 | Bosman | ........................ | 128/849 |
| 5,106,629 A | 4/1992 | Cartmell et al. | | |
| 5,941,907 A * | 8/1999 | Augustine | ..................... | 607/104 |
| 6,345,623 B1 * | 2/2002 | Heaton et al. | ................ | 128/897 |
| 6,395,955 B1 | 5/2002 | Roe et al. | | |
| 6,685,681 B2 | 2/2004 | Lockwood et al. | | |
| 6,820,622 B1 * | 11/2004 | Teves et al. | ................... | 128/849 |
| 6,979,324 B2 | 12/2005 | Bybordi et al. | | |
| 7,117,869 B2 * | 10/2006 | Heaton et al. | ................ | 128/897 |
| 7,645,269 B2 | 1/2010 | Zamierowski | | |
| 7,723,560 B2 | 5/2010 | Lockwood et al. | | |
| 7,825,289 B2 | 11/2010 | Vess | | |
| 7,886,746 B2 * | 2/2011 | Heaton et al. | ................ | 128/897 |
| 7,896,856 B2 | 3/2011 | Petrosenko et al. | | |
| 7,910,791 B2 | 3/2011 | Coffey | | |

(Continued)

FOREIGN PATENT DOCUMENTS

| | | |
|---|---|---|
| GB | 1128166 | 9/1968 |
| WO | WO/2005/047792 | 5/2005 |
| WO | WO/2005/105176 | 11/2005 |

OTHER PUBLICATIONS

Korean Search Report dated Jul. 11, 2014 issued in PCT/US2014/024636.

*Primary Examiner* — Patricia Bianco
*Assistant Examiner* — Raymond E Harris
(74) *Attorney, Agent, or Firm* — Blank Rome LLP

(57) ABSTRACT

The present invention relates to surgical safety drapes that are provided with a mechanism for removing fuel sources, trapped under the surgical drape covering the patient during surgery, which support the generation of operating room fires. The drape contains a plenum layer that is sandwiched between a liquid impervious layer and a porous layer. The plenum layer contains hollow members for providing a path way for evacuating vapors there through via the porous layer.

18 Claims, 7 Drawing Sheets

(56) References Cited

U.S. PATENT DOCUMENTS

| | | | |
|---|---|---|---|
| 7,976,519 B2 | 7/2011 | Bubb et al. | |
| 8,021,347 B2 | 9/2011 | Vitaris et al. | |
| 8,034,038 B2 * | 10/2011 | Biggie et al. | 604/319 |
| 8,048,046 B2 | 11/2011 | Hudspeth et al. | |
| 8,057,447 B2 | 11/2011 | Olson et al. | |
| 8,080,702 B2 | 12/2011 | Blott et al. | |
| 8,147,468 B2 | 4/2012 | Barta et al. | |
| 8,152,785 B2 | 4/2012 | Vitaris | |
| 8,162,907 B2 | 4/2012 | Heagle | |
| 8,162,909 B2 | 4/2012 | Blott et al. | |
| 8,167,856 B2 | 5/2012 | Kazala et al. | |
| 8,188,331 B2 | 5/2012 | Barta et al. | |
| 8,207,392 B2 | 6/2012 | Haggstrom et al. | |
| 8,246,591 B2 | 8/2012 | Braga et al. | |
| 8,257,328 B2 | 9/2012 | Augustine et al. | |
| 2002/0128578 A1 * | 9/2002 | Johnston et al. | 602/43 |
| 2004/0225341 A1 | 11/2004 | Schock et al. | |
| 2006/0264796 A1 * | 11/2006 | Flick et al. | 602/48 |
| 2007/0185463 A1 | 8/2007 | Mulligan | |
| 2007/0225663 A1 | 9/2007 | Watt et al. | |
| 2008/0053462 A1 * | 3/2008 | Teves et al. | 128/849 |
| 2008/0103462 A1 | 5/2008 | Wenzel et al. | |
| 2008/0139987 A1 * | 6/2008 | Ambrosio et al. | 602/43 |
| 2009/0312723 A1 | 12/2009 | Blott et al. | |
| 2010/0036334 A1 | 2/2010 | Heagle et al. | |
| 2010/0160877 A1 | 6/2010 | Kagan et al. | |
| 2010/0174250 A1 | 7/2010 | Hu et al. | |
| 2010/0262094 A1 | 10/2010 | Walton et al. | |
| 2010/0263678 A1 | 10/2010 | Baumann | |
| 2010/0300708 A1 | 12/2010 | Raphael et al. | |
| 2011/0009838 A1 | 1/2011 | Greener | |
| 2011/0087179 A2 | 4/2011 | Blott et al. | |
| 2011/0112492 A1 | 5/2011 | Bharti et al. | |
| 2011/0213319 A1 | 9/2011 | Blott et al. | |
| 2012/0071841 A1 | 3/2012 | Bengtson | |
| 2012/0095419 A1 | 4/2012 | Riesinger | |
| 2012/0143113 A1 * | 6/2012 | Robinson et al. | 602/43 |
| 2012/0157945 A1 | 6/2012 | Robinson et al. | |

* cited by examiner

SURGICAL DRAPE WITH VAPOR EVACUATION

FIELD OF THE INVENTION

The present invention relates generally to surgical drapes and uses therefor. The surgical drapes of the present invention are provided with a mechanism for removing trapped fuel sources, under the surgical drape covering the patient during surgery, which support the generation of operating room fires.

BACKGROUND OF THE INVENTION

Surgical drapes are used during medical procedures to create and maintain a sterile environment about the surgical site. Draping materials are selected to create and maintain an effective barrier that minimizes the passage of microorganisms between non-sterile and sterile areas. To be effective, a surgical drape barrier material should be resistant to blood, aqueous fluid, and abrasion, as lint-free as possible and drapable. When used during surgery, drapes prevent blood and other bodily fluids from contaminating the sterile field.

Various types of surgical drapes have been used to keep a surgical site on a patient sterile during a surgical procedure. Disposable drapes are usually employed. A typically disposable drape includes a two layer system: an absorbent underside layer that is directed against the patient's skin, and a liquid-impermeable layer that is constructed on top of and fixed, with adhesive, to the absorbent layer to create a two layer surgical drape. A reinforcement area is often placed around a fenestration to provide structural strength and/or to absorb fluids from the surgical site. An adhesive material may be attached to the periphery of the drape material about the fenestration to hold the drape in place around the surgical site and to minimize the passage of blood/fluids between the drape and the patient's body at the edge of the surgical opening. The combination of the drape itself and the adhesive material around the perimeter of the aperture provides for a barrier between the surgical wound and the remainder of the body. Many of today's surgical drapes are made of disposable nonwoven fabrics, plastic film, or papers.

Prior to operation, a patient is positioned upon an operating room table; and the skin surrounding the operative site is sterilized, usually with a solution containing at least 70% isopropyl alcohol. This concentration of alcohol has been tested as superior as to its rapid bactericidal properties in killing bacteria within minutes. Therefore, a necessary consequence of this disinfectant process in sterilizing the surgical site is the introduction of a compound into the operating room that is a volatile fuel for fires in and about the surgical patient and operating room staff. This fire catastrophe with disinfectant alcohol as the primary fuel occurs hundreds of times per year in the United States alone and results in significant patient death and burn injuries. Hundreds of patients annually suffer disfigurement, especially about the head and neck, resulting from burns associated with these surgical fires. Operating room physicians and other operating room staff have also received burn injuries in this circumstance and this represents a serious workplace hazard according to standards organizations and fire prevention organizations. Burns and other injuries suffered in these fires result in significant medical malpractice litigation and cost issue.

The operating room procedure for sterile prepration of the incision site is significant in the potential for fire as a necessary consequence of the surgical site sterile prep technique. The surgical drapes are specifically designed for specific types of operations, with the drape surgical opening, or fenestration of the usual size required for the designed procedure. However, it is common, without prior notice, in most procedures for the surgeon to have to enlarge the surgical site opening in the drape for greater access or to expand the operation. In this circumstance, the surgeon will cut the drape at the fenestration to enlarge it for a greater or different incision. The surgical prep personnel, aware of this possibility, routinely prep a larger skin area much larger than the usual surgical drape opening to insure that they have a sterile prep area larger than the surgical site opening in case the surgeon decides to cut the drape opening and enlarge the surgical site. Therefore, at the end of the alcohol prep, as the skin is drying from the evaporating alcohol, the surgical drape is applied with the drape surgical site over the proposed incision. Even though the skin appears to be drying, significant evaporation of alcohol is still occurring at the surgical site. Evaporation of prep alcohol is also still occurring in the area larger than the drape fenestration. However, this area is now placed under the drape that is now applied, and the alcohol molecules evaporating in this area, now under the drape at the edge of the surgical drape opening, cannot escape through the impervious drape applied. It is in this area, just at the edge of the surgical drape opening, and extending to the limits of the expanded prep area, where dangerous accumulations of alcohol molecules occur through evaporation. All that is now needed for the development of fire is an ignition spark. This is provided by the surgeon at the beginning of the procedure to provide for electrical coagulation of bleeding during the skin incision with the standard electrocautery. Fuel, oxygen and ignition equals the triad of fire. An additional hazard is that alcohol burns with a colorless flame, so that the resultant fire may not be apparent until the drape, now burning, changes color, delaying recognition of the burn damage occurring to the usually anesthetized patient's skin surrounding the incision site. This is the primary mechanism of operating room fires. The addition of supplemental oxygen by the anesthesiologist due to patient needs is a further oxidant that speeds and enriches the fire. However, in the presence of high alcohol molecule concentrations, the fire will proceed rapidly even without additional oxygen supplied and rapid fires occur with just room air. Because much of the supplemental oxygen provided to the patient is located in the neck and head area, 62% of all surgical fires occur in the head, neck, chest, and airway areas.

For a fire to occur, three elements must be present: a fuel source, oxygen, and an ignition source. As noted above, all those elements may be present during surgery, particularly in the head, neck, and chest area. Since electrosurgical cautery is a well established surgical tool to decrease blood loss, fire prevention in the operating room involves removal of the other elements of fire from the surgical area, the fuel, concentrated alcohol, and any high oxygen concentration.

Therefore, there remains a critical need for a surgical drape that contains a mechanism for removing alcohol vapors and high oxygen concentrations trapped under the drape, thereby removing that fuel source from the surgical area and minimizing operating room fire potential and patient/medical staff injury. Such an surgical drape will reduce the workplace hazards associated with high concentration alcohol prep solutions and their fire danger. The overall hazards to patients and operating room staff will be significantly reduced. Patient and staff injuries as a result of operating room fires will be reduced significantly.

SUMMARY OF THE INVENTION

Accordingly, the present invention defines provides novel multifunction surgical drape design for use during surgical procedures incorporating increased patient safety considerations and other advantages provided during surgical procedures. Because it incorporates multiple structural advances and purposes important to the patient and to the surgical procedure, the surgical drape of the present invention is also referred herein as the "surgical safety drape" which is provided with structural and functional advances over presently existing surgical drapes.

An object of the present invention is to provide a surgical drape having a mechanism for evacuating vapors with high fire producing potential. The surgical safety drapes are particularly useful for evacuating vapor trapped between the drape and a patient's skin during surgery. The surgical safety drape of the present invention contains a liquid-impervious layer, a porous layer, and plenum layer (middle layer) sandwiched between the impervious layer and the porous layer. The plenum layer contains hollow members for providing a path way for evacuating vapors there through via the porous layer. Preferably, the hollow members are preferably hollow evacuation lines with openings on their walls and/or hollow balls with holes thereon. Preferably, the one mono-layer of hollow members is sandwiched between the layers for efficient gas evacuation. The surgical drape of the present invention significantly reduces the likelihood of fire during surgical operations by removing the fuel source from the space between the patient's skin and the drape.

Another object of the present invention is to provide a method for making a surgical drape having a mechanism for evacuating vapors. The method includes providing a liquid-impervious layer and a porous layer, and sandwiching a mono player of hollow members between the two layers to provide a pathway for evacuating vapors through the porous layer.

Another objection of the present invention provides a method for using a surgical drape having a mechanism for evacuating vapors. The method includes placing the surgical drape of the present invention over a patient and applying a vacuum to the hollow members such that the space between the two layers is under negative pressure to evacuate vapors trapped between the patient's skin and the drape.

The surgical safety drape of the present invention is designed with ventilation ports throughout the drape structure in its middle layer that provide for evacuation of fire producing and fire supporting gases accumulated during the surgical preparation procedure where highly concentrated and flammable alcohol and other flammable disinfectant agents are used.

This surgical drape also contains an apparatus to allow for change of its flexibility and conformation in desired areas in order to provide stability and protective resistance against instruments placed on the drape above to protect the patient body surface beneath the drape from pressure injuries.

This surgical drape is also designed to take advantage of the ventilation capabilities of its structure via its ventilation ports by providing inherently, within its internal structure, a mechanism for positive, forced-warm-air heating of portions of the drape covering the patient's body. This application can occur after the conclusion of the surgical preparatory period, and after the volatile and flammable disinfectant agents have been evacuated via the ventilation mechanism of the surgical safety drape.

Listed below are the Standards that are employed in the design and construction of the surgical safety drape:

1. NFPA Standards—Standards for the Use of Inhalation Anesthetics
2. ASTM ES-21-1992, Standard Test Method for Resistance of Protective Clothing Materials to Synthetic Blood.
3. ASTM ES-22-1992, Test Method for Resistance of Protective Clothing Materials to Penetration by Bloodborne Pathogens Using Viral Penetration as a Test System.
4. ASTMD737-75, Air Permeability.
5. AATCC Test Method 127-1989, Water Resistance: Hydrostatic Pressure Test (water resistance claims).
6. AATCC Test Method 61-1989, Colorfastness to Laundering, Home and Commercial: Accelerated.
7. ASTM D1424, Elemendorf Tear.
8. ASTM D1682, Grab Tensile/Elongation

DETAILED DESCRIPTION OF THE PREFERRED EMBODIMENTS

Figure 1:
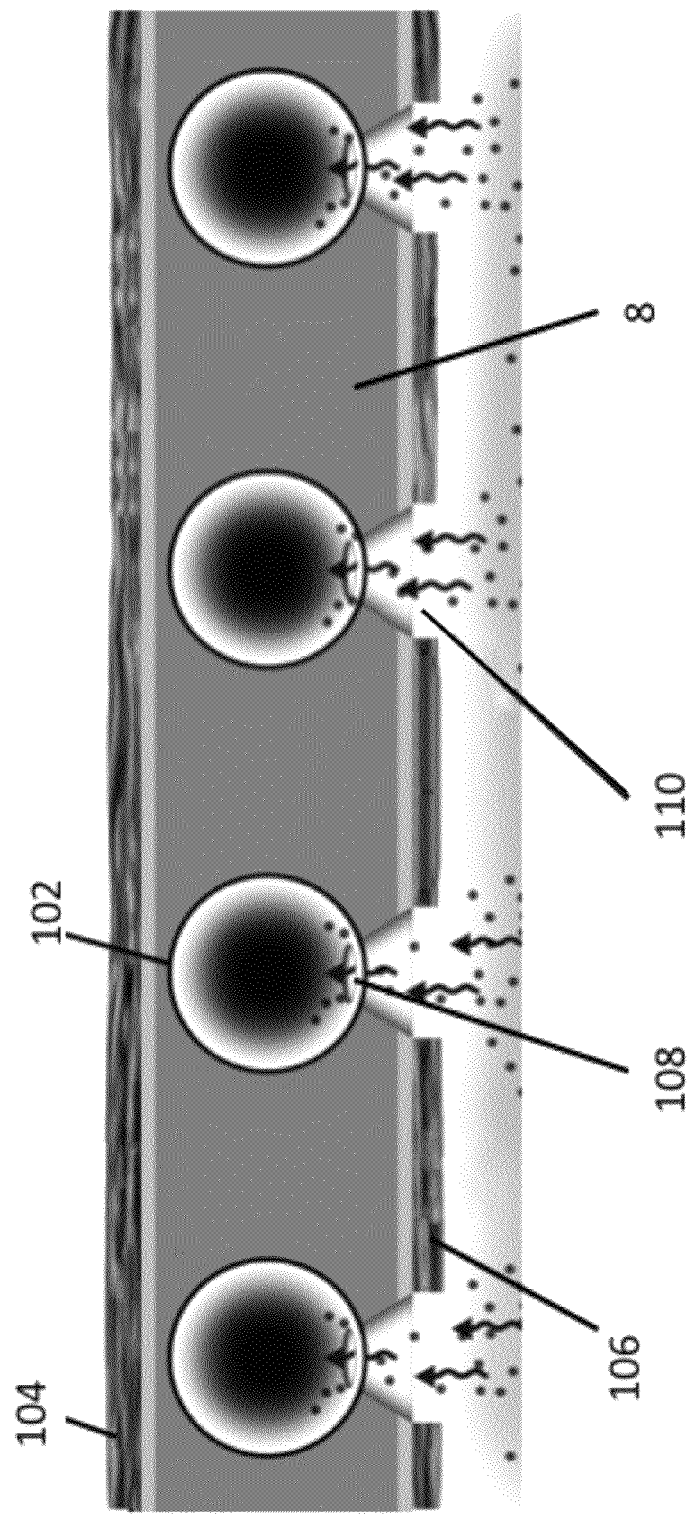
FIG. 1 is a drawing showing a cross-section (perpendicular to the channels) of one embodiment of the surgical safety drape of the present invention.

The present invention relates to surgical drapes having a mechanism for evacuating vapors, preferably fire producing and supporting vapors. The drapes are particularly useful for evacuating vapor trapped between the drape and a patient's skin during surgery. The surgical drape contains a liquid-impervious layer, a porous layer, and hollow members sandwiched between the two layers to provide a pathway for evacuating vapors through the porous layer.

The impervious and porous layers of the present invention can be made of components similar to commercially available disposable surgical drapes. These two components render this drape impervious to blood, fluids and bacteria. In this respect, this drape is similar in construction to many of the surgical drapes presently with full FDA approval and now being marketed. This construction is calculated to allow for successful completion of the FDA test battery for surgical drape approval. The middle of the drape between the two layers (also referred herein as the plenum layer), not in contact with the patient or open to the surgical field that provides its unique fire prevention vapor aspiration and ventilation capabilities, is composed of chemically biocompatible components with modifications allowing for increased structural integrity. These components are similarly biodegradable and do not represent a hazard to the environment, breaking down on incineration to carbon dioxide and water. These components also give sufficient strength to this drape sufficient to resist tearing with heavy surgical instruments. The additional ability of this drape to increase the rigidity and support capabilities in desired drape sections due to conformational changes induced in the plenum layer during the procedure also provides an additional margin of patient safety by modification of certain drape sections placed over critical patient body structures to resist the effect of heavy instruments compressing patient body structures beneath the drape. The plenum layer conformational change can also provide a reinforcement area around the surgical site opening (fenestration) in the drape to provide structural strength. An adhesive material is attached to the edge of the surgical field opening in the drape material to hold the drape in place around the surgical site and to minimize the passage of blood/fluids between the drape and the patient's body. The combination of the drape itself and the adhesive material around the perimeter of the surgical field usually provides a barrier between the surgical wound and the non-sterile remainder of the patients' body. The impervious layer of the surgical drape is generally composed of a laminate, e.g. of polypropylene, polyurethane, and/or polyethylene materials or other similar non-toxic, biocompatible compounds.

The porous layer of the surgical drape may be made of the same material as the impervious layer but with pores built into the material connecting into the plenum layer. This porous layer is on the underside of the drape (when in use is in contact with the patient's skin) where the pores, open to the underside of the drape, provide a conduit for removal of the vapors above the patient's skin. These pores are important in providing a path for the evacuation of the fuel source on the patient's skin.

The impervious and porous layers provide a plenum layer that is sandwiched between the impervious and porous layers. That plenum layer contains structures unique to this invention that incorporate ventilation channels within the drape thickness to allow for gas movement through the structure of the drape itself, a mechanism for evacuating vapors that are trapped between the underside of the drape and the patient's skin when the surgical drape is in use. In accordance to the present invention, this plenum layer is provided beneath the impervious layers to provide the evacuation mechanism. Beneath the plenum layer is the porous layer containing ventilation pores open to the underside of the drape and fluidly connecting, through the porous layer, up to the plenum layer, which allow for movement of gases from the underside of the drape to the structures in the plenum layer for removal via the plenum layer. The plenum layer provides mechanisms for evacuating vapors that are trapped between the porous layer and the patient's skin when the surgical safety drape is in use. In accordance with the present invention, a hollow member is provided between the two layers (the plenum layer) to provide the evacuation mechanism Referring to FIGS. 1 and 2, in one embodiment of the present invention, the mechanism for evacuating vapors includes multiple channels 102, between the impervious layer 104 and the porous layer 106. The porous layer having pores 110. Each of the channels 102 has ports 108 on its wall to provide fluid communication with the space 8 between the two layers 104 and 106, and with the pores 110. The channels 102 can be formed by, e.g. tubes placed between the two layers 104 and 106. Preferably, the channels 102 are placed such that only one tube separating the two layers 104 and 106. Multiple stacking of the channels 102 is to be avoided as that would add to the thickness of the drape without providing additional evacuation benefit. The ports 108 of the channels 102 are preferably oriented toward the porous layer 106 (facing the porous layer 106) to facilitate evacuation of gases through the porous layer 106 and into the channels 102, when a vacuum is applied to the interior of the channel.

Figure 2:
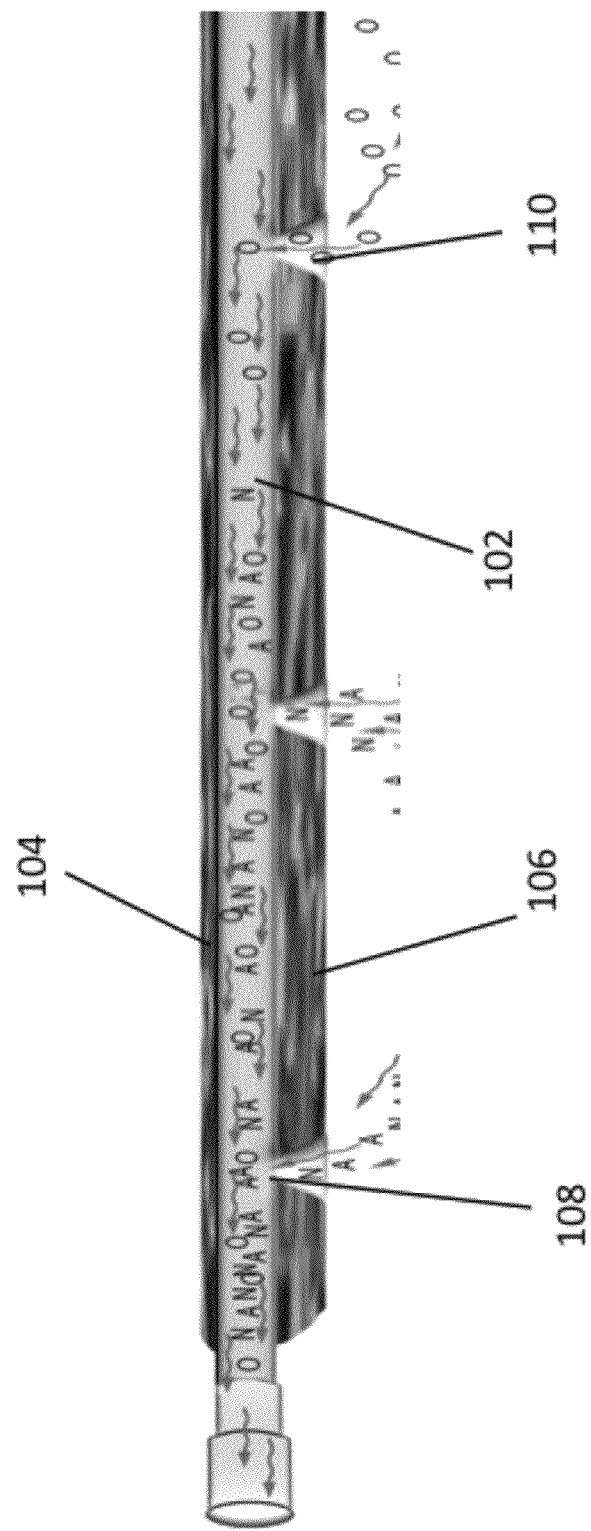
FIG. 2 is a drawing showing a cross-section (parallel to the channels) of the embodiment shown in FIG. 1.

The channels 102 can be constructed of various polymers, such as polyurethane, polyethylene, or polypropylene. Alternatively, the space 8 between layers 104 and 106 is filled with a thermally insulating gel and the channels 102 are formed by elongated voids within the gel. In any event the gel should not block fluid communication between the pores 110 and the ports 108. The gel can be, but is not limited to, polyurethane, polyethylene, polypropylene, and/or other formulations having the required structural and flexible characteristics. In this case, the ports 108 are formed on the surface of the channels 102. Preferably, the ports are formed such that they face the porous layer 106 directly, as shown in FIG. 1. The material used (gel or channel) should be sufficiently flexible to allow the surgical safety drape to conform to the patient's body shape when in use, without impediment to the surgical team. At the same time, the channels 102 have structural characteristics such that they remain open for the vacuum aspiration and ventilation functions.

The channels 102, when in use, are connected to a vacuum source, such as a vacuum pump, that can be used to apply a vacuum to the channels. Preferably, the channels are connected in series or in parallel to a common vacuum source at the edge of the surgical safety drape. The vacuum applied should be sufficient to quickly withdraw gas through the porous layer 106 without collapsing the channels 102. Likewise, the channels 102 should have sufficient rigidity to withstand the applied vacuum. For a typical surgical drape, the vacuum applied is about 25 to about 150 cm of $H_2O$, more preferably about 50 to about 75 cm of $H_2O$. Preferably, the channels 102 are laterally separated from each other by a distance (center to center) of about 3 to about 7 mm, more preferably about 4 to about 6 mm.

Figure 3:
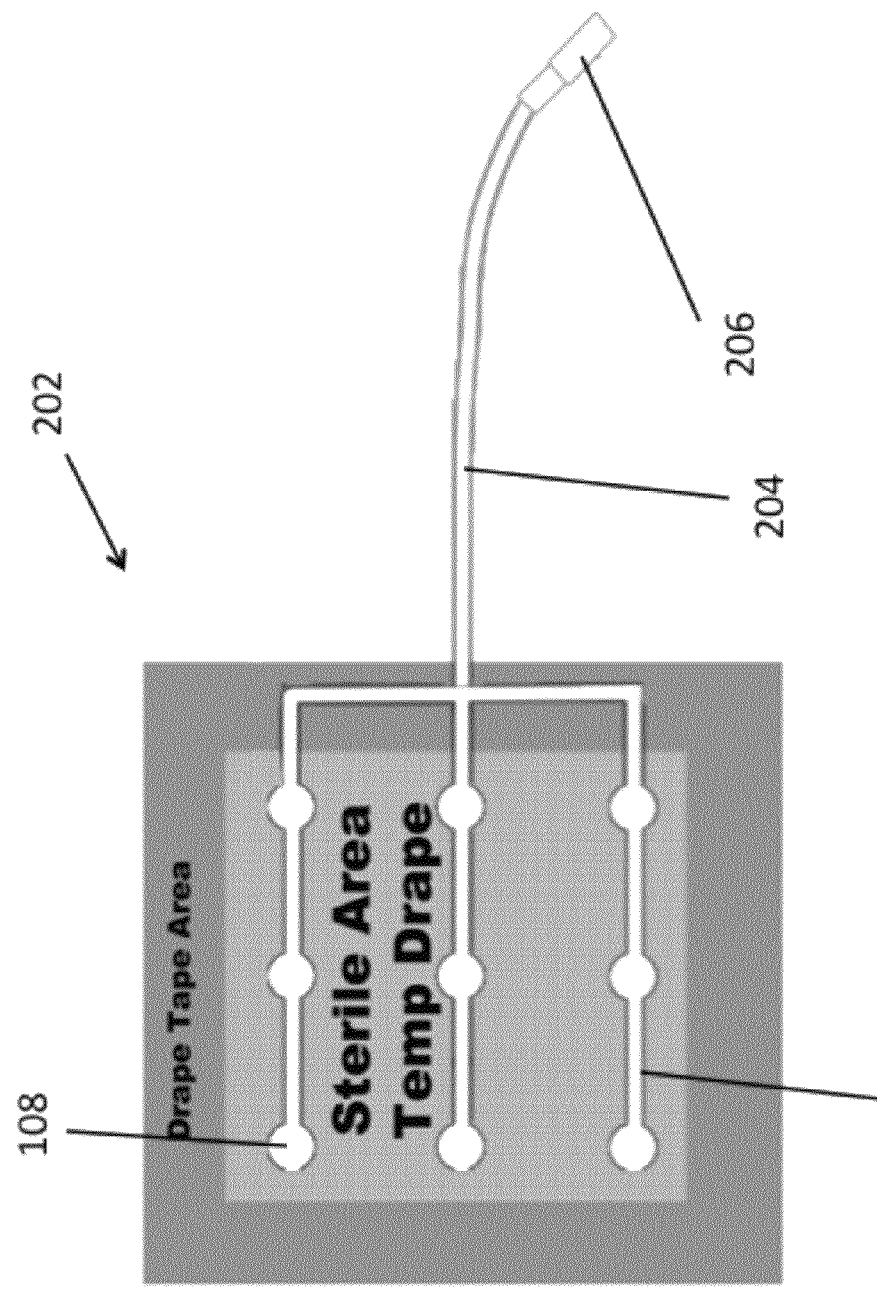
FIG. 3 is a drawing showing a top view of the embodiment shown in FIG. 1.

FIG. 3 shows a top view of the drape 202 having multiple channels 102 therein. Here, the channels 102 are lead to a main aspiration tube 204 that is designed to be removably connected to a vacuum source via a connector 206. The connector 206 can be various vacuum connectors known in the art, such as push-pull connectors with self locking mechanisms. In certain embodiments, the surgical safety drape also includes a portion that is designed to aspirate directly over the surgical drape opening (fenestration) where the surgical incision is contemplated. Its purpose is temporary, and is to provide for fast removal and drying of the disinfectant prep solution directly over the surgical site. After a few minutes of vacuum aspiration directly over the surgical site, this portion of the surgical safety drape is preferably detached from the remainder of the safety drape, which is kept in place. This detachment leaves a dry surgical incision site ready for surgery yet remaining sterile and free of flammable vapors. This process promotes faster drying of the surgical site and decreases the operating room wait time for surgical disinfectant drying after sterile surgical prep.

Figure 4:
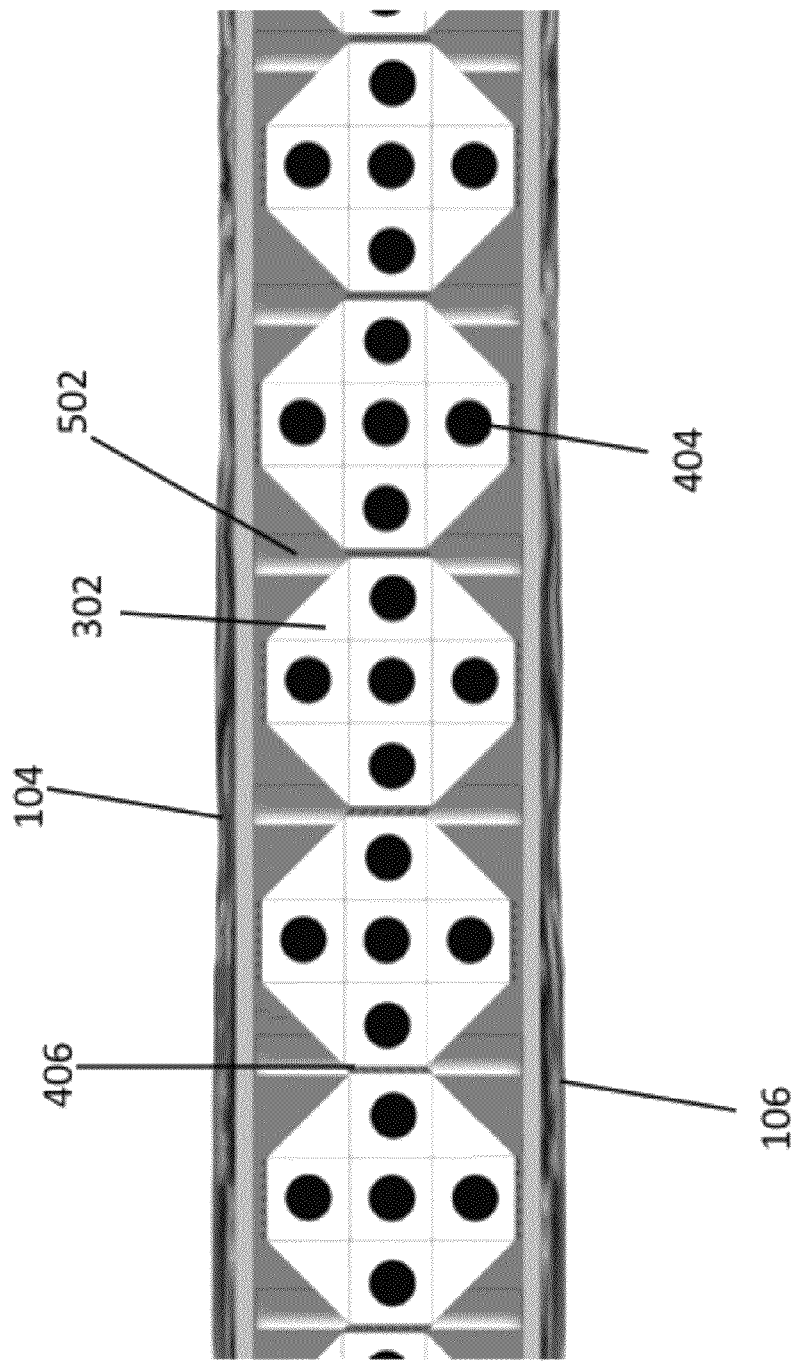
FIG. 4 is a drawing showing a cross-section of another embodiment of the surgical safety drape of the present invention.
Figure 5:
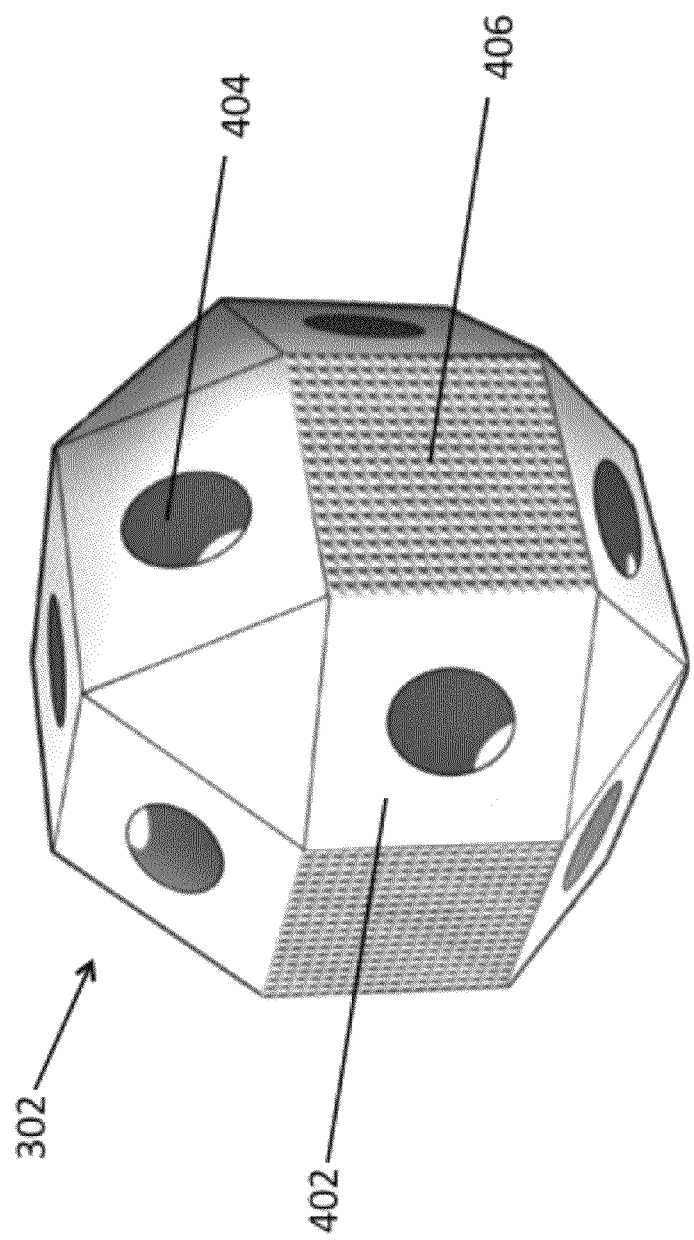
FIG. 5 is a drawing showing the polygonal ball used in the embodiment shown is FIG. 4.
Figure 6:
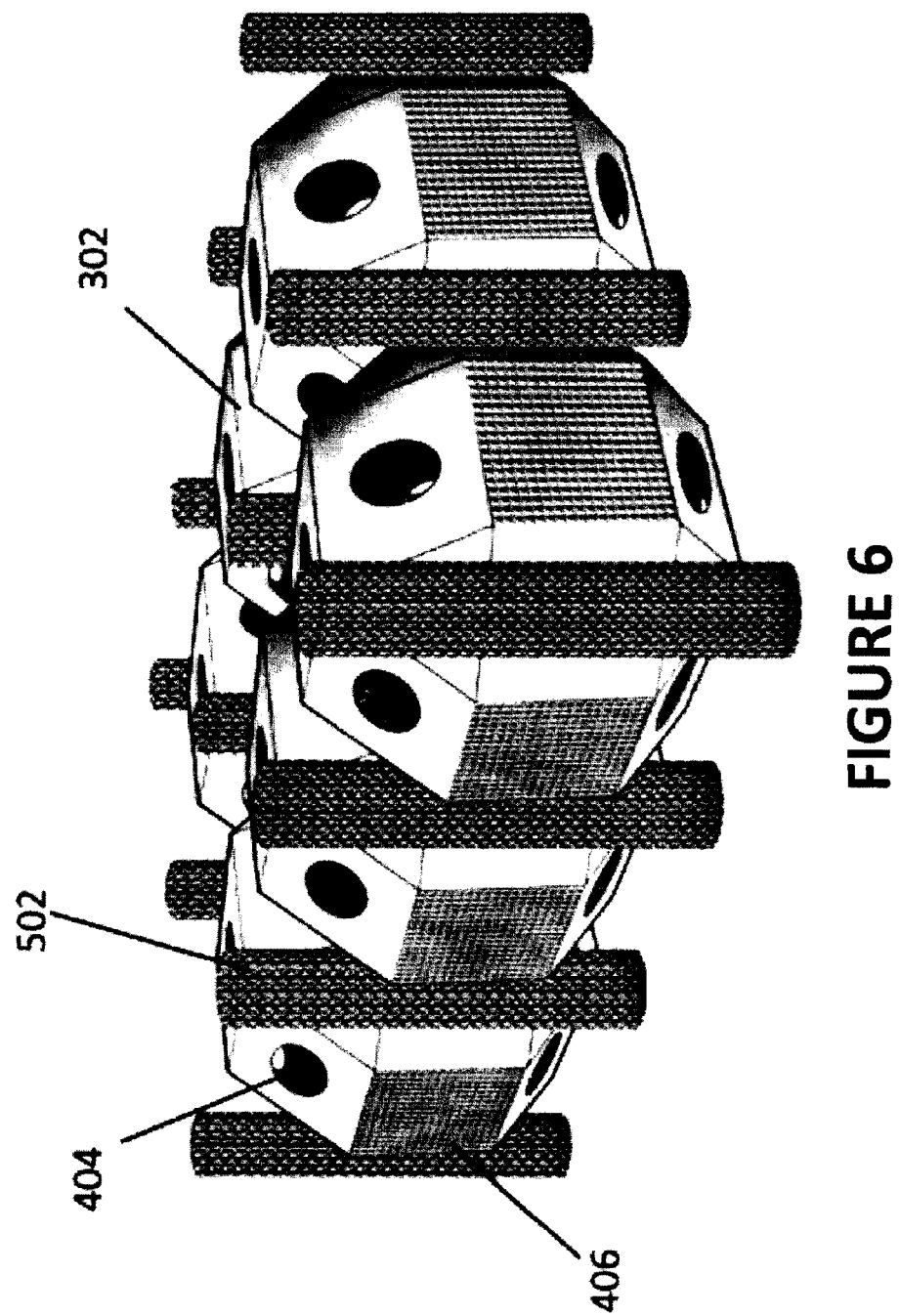
FIG. 6 is a drawing showing the composition of the plenum layer of the embodiment shown is FIG. 4.

Referring to FIGS. 4-6, in another embodiment, the mechanism for evacuating vapors includes a plurality of hollow balls 302 having holes thereon to allow free passage of gas therethrough. Importantly, to preserve the functionality of the surgical drape, there should only be one monolayer of balls in between the impervious layer 104 and the porous layer 106. In this case, when a vacuum is applied between the two layers 104 and 106, gas is evacuated through the porous layer 106. Each ball has rigidity sufficient to withstand the vacuum force applied between the two layers. However, in practice, as shall be apparent below, it is preferred that the rigidity of the balls is much higher than that just sufficient to withstand the force due to the supplied vacuum. The balls may be constructed from the following materials: polycarbonate, polypropylene, or polyurethane. Desirably, the balls are made sufficiently stiff to withstand being crushed by surgical objects placed on to the surgical safety drape. The crushing pressure on the ball should be greater than about 5 PSI.

Referring to FIG. 5, each ball is preferably composed of a plurality of polygonal surfaces 402, where at least some of the surfaces 402 have holes 404 there on. The ball preferably has a diameter or longest distance between opposing surfaces of about 1 to about 5 mm, more preferably about 2 to about 4 mm. Further, abutting surfaces 406 on adjacent balls are preferably roughened or contain corrugations to allow the balls to lock together to form a rigid surface as shall be apparent below. Each of the abutting surfaces 406 preferably contains raised, interlocking pyramids on its surface (as illustrated in FIG. 5). When under vacuum suction, preferably maintained constantly after initiation, the pyramidal like surfaces on the face of the polygons interlock due to slight movement (less than 0.5 mm) of the polygons, preventing the polygons to then move in any direction relative to each other, resulting in adjacent polygons to lock together to form and act collectively as a single rigid structural surface. This interlocking feature of the activated rigidity section can be applied to vertical as well as horizontal rigidity as required in surgical safety drape design.

FIG. 6 show a preferred construction of the embodiment of the present invention with hollow balls 302. First, the balls 302 are aligned in a monolayer. Vertical plenum columns 502 are placed in spaces between the balls 302 to confine each balls to a particular position in the plenum layer. The top and bottom of the plenum layer are then capped with the impervious layer 104 and the porous layer 106 (as illustrated in FIG. 4). The top and bottom of the plenum columns 502 are attached permanently to the two layers, respectively. The plenum columns 502 are positioned such that the balls 302 are kept relatively in place and to prevent movement of the balls, particularly not allowing the balls to stack on top of one another. This way, the monolayer of balls is maintained throughout the surgical drape. Each of the plenum columns preferably has a circular cross-section with a diameter of about 0.25 to about 1.25 mm, more preferably about 0.5 to about 1 mm. The plenum columns 502 are preferably sufficiently flexible to allow slight movement in the balls 302 to allow them to come in direct contact with each other when a vacuum is applied, and to come apart when the vacuum is released. The movement of the ball should be no more than about 2 mm, preferably no more than about 0.5 mm. The plenum columns 502 can be manufacture using polymeric materials, such as polyurethane, polypropylene, or combinations thereof. Surrounding the balls in the middle plenum layer may be just air space, or in certain embodiments, may be gel-like compound composed also of formulations, such as polyurethane and polypropylene, that render the balls enclosed in a sealed plenum compartment wherein the only conduits for gas movement are the perforations in the balls allowing transmission of a vacuum effect from ball to adjacent ball when a vacuum is induced to the plenum layer.

The top and bottom ends of the plenum columns 502 are permanently anchored to the impervious layer 104 and the porous layer 106, respectively. This can be accomplished many different ways. In certain embodiments, those ends are directly attached to the layers 104 and 106 using, e.g. a glue. Alternatively, the columns can be molded as part of a large sheet, where the sheet is then attached to impervious 104 and porous 106 layers. Preferably, the attachments occur using a using a flexible glue that does not increase the stiffness of the over surgical drape.

The use of the hollow balls has the advantage of being able to provide stiffness to the surgical drape when a vacuum is supplied. Here, the balls, when not under vacuum, are sufficiently separated from adjacent balls, such that they allow the surgical drape to be flexible. However, when a vacuum is applied, the balls, because they are constrained by the plenum columns 502 come into contact at their abutting surfaces 406. The corrugations at the abutting surfaces 406 allow the balls to lock together, thereby producing a stiff surgical drape. The stiffness of the drape allows it to form a surface for the surgeon to place equipments without putting undue pressure, by weight, on the patient. The equipment can be cameras, forceps, probes, etc. The stiff surface distributes the pressure over the entire area covered by the drape, rather than allowing localized pressure, which reduces discomfort to the patient.

Figure 7:
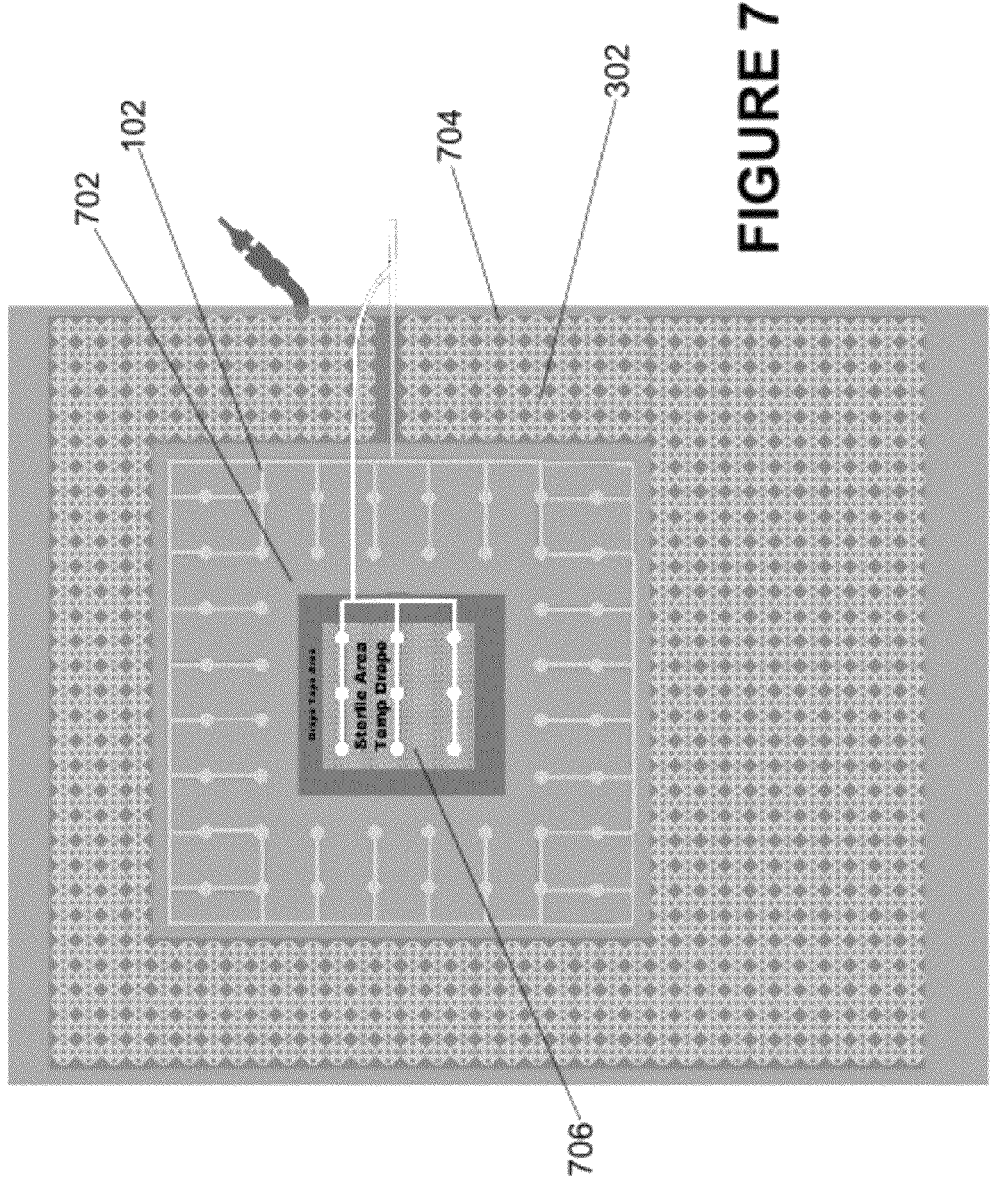
FIG. 7 is a drawing showing a surgical safety drape using a combination plenum layer.

A surgical drape of the present invention may incorporate both the hollow balls and the evacuation channels disclosed above. For example, hollow balls are used in portions of the drape where stiffness is required, while the evacuation channels are used in portions where flexibility under vacuum is required. FIG. 7 shows an embodiment of the present invention where the areas 702 closest (within about 50 to about 100 cm) to the fenestration uses the evacuation channels 102, while portions 704 beyond this area uses the hollow balls 302. Indeed, FIG. 7 shows that the fenestration, itself, contains a temporary sheet 706 that included evacuation channels 102. This temporary sheet 706 is used to evacuate vapors in that area and is removed just before the surgeon is ready to perform the surgery. The portions 704 furthest away from the fenestration uses hollow balls to effect evacuation of vapors during surgery. In particular, stiffness is desirable during surgery in portion 704 to provide a surface for the surgeon to place equipment for ready access.

In use, the surgical drape of the present invention is placed over an area of the patient with the porous layer 106 toward the skin of the patient. The drape is then connected to a vacuum source to apply a vacuum to the plenum space ventilation section between impervious layer 104 and the porous layer 106. The vacuum removes any flammable fuel trapped between the surgical drape and the patient to minimize fire risks to the patient during surgery. The vacuum need not be on during surgery after sufficient time is elapsed to assure no further evaporation of alcohol is occurring. Once the fuel source is completely evacuated (approximately 5-15 minutes), the vacuum aspiration can be turned off. If needed, the vacuum can be activated to lock the balls 302 together to form a rigid surface for placement of equipment.

In an alternative embodiment, the surgical safety drape of the present invention can also be used as a warming blanket. In this case, the air flow is simply reversed and warm air is blown on to the patient's skin. In this embodiment, warming of the patient can be controlled by providing the patient with warmed gas blown through the surgical safety drape and onto the patient's skin. For example, a warmed gas, preferably at about 36 to 60° C., more preferably about 38 to about 40° C., and most preferably about 38° C., is provided to the patient by pumping the warm gas, preferably air, through the surgical safety drape plenum layer and though the porous layer to the patient's skin. Preferably, temperature control is used for managing the temperature of the gas to warm the body to normal temperature or for treatment of certain conditions, such as hypothermia commonly found under general anesthesia.

To provide thermoregulation, the system of the present invention further requires the ability to reverse the flow of the vacuum. Alternatively, the surgical safety drape can be plugged directly to a pump to provide warm air. In any event, the system for providing warm gas includes a pump and a control system to control the temperature of the gas and to adjust the temperature of the gas. The system to modify the gas temperature can be a simple heating element placed in the path of the gas flow. That heating and/or cooling element can be controlled directly by a system which heats or cools the temperature of the gas depending on a set temperature. During operation, a desired temperature is set on the controller, which is connected to a temperature sensor placed in the flow path of the gas. Depending on the temperature of the gas, the controller activates the heating element to heat the gas. If the gas temperature is lower than the desired temperature, the controller activates the heating element to heat the gas until the desired temperature is reached. At its simplest, the controller can heat the gas based on binary control. However, sophisticated controllers can be programmed to control the rate of heating based on the difference between the desired temperature and the gas temperature.

Although certain presently preferred embodiments of the invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What is claimed is:

1. A surgical drape comprising
   an impervious layer;
   a porous layer having pores therein; and
   a plenum layer between the impervious and porous layers, the plenum layer contains
   hollow balls having holes thereon.

2. The surgical drape of claim 1, wherein the balls have abutting surfaces that are roughened or contain corrugations to allow the balls to lock together when under vacuum.

3. The surgical drape of claim 2, wherein the corrugations are raised pyramids on the abutting surfaces.

4. The surgical drape of claim 1, wherein the plenum layer further contains a gel.

5. The surgical drape of claim 1, wherein the impervious layer and the porous layers are made from flexible polyurethane, polypropylene, or polyethylene formulations.

6. The surgical drape of claim 1, wherein the hollow balls are polygonal balls having holes on some of their surfaces.

7. The surgical drape of claim 1, wherein the balls are made of polycarbonate, polyethylene, polypropylene, or polyurethane formulations.

8. The surgical drape of claim 1, wherein each of the balls are positioned between plenum columns to hold the ball in place.

9. The surgical drape of claim 1, wherein portions adjacent to a fenestration contains the channels, while portion further away from the fenestration contains the hollow balls.

10. A method for operating a surgical drape comprising the steps of
    a) providing the surgical drape of claim 1;
    b) placing the surgical drape on top of a patient;
    c) connecting the surgical drape to a vacuum source; and
    d) applying vacuum to the plenum layer to evacuate any flammable fuel source under the surgical drape.

11. The method of claim 10, wherein the balls have abutting surfaces that are roughened or contain corrugations to allow the balls to lock together when under vacuum.

12. The method of claim 11, wherein the corrugations are raised pyramids on the abutting surfaces.

13. The method of claim 10, wherein the impervious layer and the porous layers are made from flexible polypropylene, polyurethane, or polyethylene formulations.

14. The method of claim 10, wherein the hollow balls are polygonal balls having holes on some of their surfaces.

15. The method of claim 10, wherein the balls are made of polycarbonate, polyethylene, polypropylene, or polyurethane formulations.

16. The method of claim 10, wherein each of the balls are positioned between plenum columns to hold each of the balls in place.

17. The method of claim 10, wherein portions adjacent to a fenestration contains channels, while portion further away from the fenestration contains the hollow balls.

18. A method for warming a patient comprising the steps of
    a) providing the surgical drape of claim 1;
    b) placing the surgical drape on top of a patient;
    c) connecting the surgical drape to a warm air source; and
    d) blowing warm air into the plenum layer to provide the warm air to the patient.

* * * * *